United States Patent [19]

Barr et al.

[11] Patent Number: 5,354,737
[45] Date of Patent: Oct. 11, 1994

[54] FRAGRANCE COMPOSITION CONTAINING SUBSTANTIAL AMOUNTS OF ACETYL HEXAMETHYL TETRALIN, AND DEODORANT COMPOSITION CONTAINING THE FRAGRANCE COMPOSITION

[75] Inventors: Morton L. Barr, East Brunswick; Paul J. Vincenti, Jefferson; Robert V. Burke, Ridgewood, all of N.J.

[73] Assignee: The Mennen Company, Morristown, N.J.

[21] Appl. No.: 105,806

[22] Filed: Aug. 13, 1993

[51] Int. Cl.$^5$ .............................................. A61K 7/46
[52] U.S. Cl. ...................................... 512/17; 424/65; 252/174.11
[58] Field of Search ................ 512/17, 2; 424/65; 252/174.11

[56] References Cited

U.S. PATENT DOCUMENTS

| | | | |
|---|---|---|---|
| 2,897,237 | 7/1959 | Carpenter et al. | 512/17 |
| 3,045,047 | 7/1962 | Davidson et al. | 512/17 |
| 4,304,679 | 12/1981 | Hooper et al. | 512/17 |
| 4,322,308 | 3/1982 | Hooper et al. | 252/107 |
| 4,324,703 | 4/1982 | Seldner | 252/174.11 |
| 4,352,748 | 10/1982 | Traas et al. | 512/17 |
| 4,849,400 | 7/1989 | King | 512/2 |
| 5,120,709 | 6/1992 | Cella et al. | 512/2 |
| 5,198,218 | 3/1993 | Kuznitz et al. | 424/401 |

FOREIGN PATENT DOCUMENTS

WO91/07165 11/1989 PCT Int'l Appl. ............ 252/174.11

OTHER PUBLICATIONS

Keiser, et al "Proceedings of the 1976 International Controlled Releases Pesticide Symposium", Abstract.
Gressel, et al "Safety Evaluation of Four Bicylic Musk Fragrance . . . " 1980/N. Holland Biomedical Press . . . , pp. 53–58.
Muller, et al "Understanding Fragrance. Origin, History . . . ", The H&R Book of Perfume, p. 67.
Gras "The Overdoes", vol, 15, Nov./Dec. 1990, Perfumer & Flavorist.
Gras "The Overdose II", vol. 17, Jan./Feb. 1992, Perfumer Flavorist.
"Tonalid", Hercules, Apr. 1991, (Aroma Chemicals Specification) Ref. No. 263400.
"Tonalid 2", Hercules, Apr. 1991, (Aroma Chemicals Specification) Ref. No. 263406.
"Tetralide", Bush Boake Allen Product Data, CAS Registry No. 21145-77-7.
"Tetralide 2", Bush Boake Allen Product Data.
"Tonalid" (Polak's Frutal Works).

*Primary Examiner*—James H. Reamer
*Attorney, Agent, or Firm*—Antonelli, Terry, Stout & Kraus

[57] ABSTRACT

Disclosed is a fragrance composition having enhanced efficacy for masking malodor, for extended periods of time, the fragrance composition containing fragrance materials that provide a top note and/or a middle note and/or a bottom note, and also containing more than 28%, and up to 95%, by weight, of the total weight of the composition, of acetyl hexamethyl tetralin. The fragrance composition can be incorporated in deodorant compositions to be applied to a person's skin, e.g., in axillary regions, to combat body malodor, including malodor arising in axillary regions.

38 Claims, No Drawings

FRAGRANCE COMPOSITION CONTAINING SUBSTANTIAL AMOUNTS OF ACETYL HEXAMETHYL TETRALIN, AND DEODORANT COMPOSITION CONTAINING THE FRAGRANCE COMPOSITION

BACKGROUND OF THE INVENTION

The present invention relates to a fragrance composition that is longer lasting and has enhanced efficacy; and a deodorant composition, particularly for treating body malodor (for example, malodor arising in axillary regions of the human body, due to, for example, bacteria acting on axillary perspiration), containing such fragrance composition. In particular, the present invention is directed to a fragrance composition, and deodorant composition containing such fragrance composition, having enhanced efficacy, and retaining, for example, the fragrance of the top note and/or middle note and/or bottom note of the fragrance composition such that the fragrance composition maintains a relatively balanced fragrance (desired bouquet) for longer periods of time.

Fragrance compositions, such as perfumes, have been used as odor maskants since ancient times, and it is conventional to incorporate fragrance compositions in body deodorants (for example, deodorants to be applied to axillary regions of the human body) in order to overcome body malodor. These fragrance compositions have been incorporated into deodorants together with other deodorant active materials, such as, for example, bacteriostats (for example, Triclosan).

Illustrative examples of deodorant compositions, to be applied to axillary regions, containing fragrance compositions are shown in U.S. Pat. No. 5,198,218 to Kuznitz, et al. This patent discloses deodorant stick compositions containing a polyhydric alcohol and gelled with a soap; and further containing a specific alkoxylate co-polymer and a fragrance to impart a pleasant odor to the composition. This patent discloses various materials (called deoperfumes) that are perfumes having deodorant properties and are classified into at least one of the following six classes:
  Class 1: phenolic substances
  Class 2: essential oils, extracts, resins and synthetic oils
  Class 3: aldehyde and ketones
  Class 4: polycyclic compounds
  Class 5: esters
  Class 6: alcohols
This patent discloses specific fragrance compositions, containing specific amounts of various defined compounds. The contents of U.S. Pat. No. 5,198,218 are incorporated herein by reference in their entirety.

However, in incorporating fragrance compositions, in, for example, deodorants, a problem arises in that the deodorant composition does not sufficiently retain its desired fragrance (aroma) for a sufficient period of time (for example, for 24 hours) after application of the deodorant to the body.

Fragrance formulation is an art in which the senses of the skilled perfumer are more important than chemical analysis. A fragrance results from a variety of components (materials) in a fragrance composition. Ordinarily, fragrances are created by blending materials (ingredients) comprising odoriferous essential oils, extracts from woods, gums, flowers and other botanicals, resins, animal secretions, and synthetic aromatic materials. These materials are blended in order to achieve what are known as "top note", "middle note" and "bottom note" components. The first is the refreshing quality sensed upon application. The last is the essence of the fragrance which stays with the wearer for a long time. The middle note is the perceived quality that bridges from top note to bottom note.

The materials themselves are each classified with respect to the aromas (odor) given off, as to providing a green note, floral note, aldehydic note, fruity note, chypre note, oriental note, leather note, tobacco note, fougère note, etc.

In the creation of fragrances, certain materials have generally been selected for their use as fragrance fixatives. These fragrance fixatives are substances which amplify fragrance ingredients long after application and improve lasting qualities of odorous substances of a fragrance. A fragrance fixative has principal activity with respect to the lasting quality and the bottom note of the fragrance. In many instances, the fragrance fixative contributes to, for example, the bottom note of the fragrance.

Various materials are available to the perfumer as fixatives, and include the following:
1. Floral and botanical absolutes, concretes and resinoids;
2. Animal secretions and extracts;
3. Macrocyclic musks;
4. Polycyclic musks; and
5. Nitromusks.

It is well known that fragrance fixatives can distort the nature or character of the fragrance being fixed. Various attempts have been made to fix the fragrance, while avoiding distortion of the nature or character of the fragrance.

One patent addressing this problem is U.S. Pat. No. 4,324,703 to Seldner. This patent discloses incorporation of certain methyl glucoside polyols, including alkoxylated methyl glucoside and particularly ethoxylated and propoxylated methyl glucoside, which are essentially odorless, as fragrance fixatives in fragrance compositions. This patent discloses that the described fixatives can be incorporated in various fragrance compositions such as perfumes, colognes, after-bath splashes, after-shaves, perfumed powders, soaps, creams, lotions and virtually every other system which can be fragranced. The contents of this U.S. Pat. No. 4,324,703 to Seldner is incorporated herein by reference in their entirety.

A disadvantage of the fragrance composition of Seldner is that it requires an additional component in the composition.

U.S. Pat. No. 5,120,709 to Cella, et al discloses another technique for providing fixatives for fragrance compositions; and, in particular, provides a technique for enhancing the quality of applied fragrances. This patent discloses that a fixative agent is co-applied with a fragrance form; and that, in a preferred technique, the fixative is independently applied to the same area as the fragrance form. As a specific embodiment, this patent discloses that the fixative agent is applied by overspraying the composition, including the fixative, in a volatile solvent, to the area in which the fragrance form has already been applied. This patent discloses that the fixative agent can be selected from either natural or synthetic fixative agents, and can be a nitromusk, or a macrocyclic, hydroaromatic polycyclic, or oxahydroaromatic compound or a combination thereof. Disclosed as preferred fixative agents are galaxolide, ethylene brassylate, 4-acetyl-6-t-butyl-1,1-dimethylindane, 11-oxahexadecanolide, musk ambrette, musk ketone, musk xylol, civetone and androstene-one or a combination thereof. This patent discloses that the addition of the fixative enhances the fragrance form so as to provide a richer and fuller aroma, perceived as being more expensive and finer by the user.

The technique disclosed in U.S. Pat. No. 5,120,709 is a relatively complex procedure, requiring a number of steps and a plurality of compositions. Such technique is impractical for applying body deodorant, for example.

Furthermore, each of U.S. Pat. Nos. 4,324,703 and 5,120,709 is directed to fragrance compositions providing a fragrance such as a cologne, and does not describe that the fragrances can be used to mask malodor, such as body malodor arising from perspiration in axillary regions.

Another patent disclosing a fragrance composition containing a fixative is U.S. Pat. No. 4,849,400 to King. This patent discloses the incorporation of a compound such as phenylxylylethane or phenyltolylethane as a fixative in known fragrances, to provide fragrance compositions which have a prolonged lasting quality and wherein the differing rates of diffusion and evaporation of the olfactory components are to some extent equalized. This patent discloses that the fragrance compositions disclosed, containing the known fragrances and the fixatives, can be utilized in perfumes, cosmetics, creams, toilet soaps, bath salts, hair preparations, deodorants, lotions, sunscreens, face powders and the like, and can be used to improve the scent of detergents, cleaning agents, disinfectants and textile finishing agents. This patent also discloses various typical fragrance formulations (including LAVENDER FANTASY, ROSE and CARNATION). This patent further provides a classification structure for fragrance compositions, and subclassifications for more popular fragrance classes. The contents of U.S. Pat. No. 4,849,400 to King is incorporated herein by reference in their entirety.

It is also known that an overload of fixative in a note is no guarantee of good retention of a scent, because substances can hinder one another in their fragrance diffusion. See J. Mueller, *The H & R Book of Perfume* (Understanding Fragrance. Origin, History, Development, Meaning) (1984), page 67.

U.S. Pat. No. 3,045,047 to Davidson, et al discloses a class of chemical compounds adapted for use as fixatives and blending agents in the manufacture of perfumes and perfumed products, the compounds being acylpolyalkyl-1,2,3,4-tetrahydronaphthalenes, most of the compounds having a pronounced musk-like odor. This patent discloses that the described compounds are synthesized readily from commercially available, inexpensive raw materials. This patent goes on to state that the 6-acetyl-1,1,4,4,-tetramethyl-7-ethyl-1,2,3,4-tetrahydronaphthalene, with two quaternary carbon atoms at positions 1 and 4, has a strong, persistent, musk-like odor. This patent further discloses that the presence of two quaternary carbon atoms in the alicyclic portion of the molecule appears to be necessary for the production of a musk-like odor.

In an article by M. Grass, "The Overdose II" in *Perfumer & Flavorist*, Vol. 17 (January/February 1992), pages 2–12, it was reported at page 4 that "Tonalide" is important in men's colognes (Fahrenheit, Dior 1988) at 11%, and used frequently in women's colognes in combination with other musks (Parfume Sacre, Caron 1990) at 5%; and that, nowadays, "Tonalide" is used in almost all laundry products, at levels, as a percentage of the fragrance, of 23% in the Ariel Ultra detergent (1989), 29% in the fabric softener Snuggle Morning Fresh (1989) and up to 30% in Tide Bleach (P&G 1989) where it is used for its great stability and substantivity.

In a U.S. patent application filed concurrently herewith (titled "Enhanced Efficacy, Long-Lasting Fragrance Composition, and Deodorant Composition, for Masking Malodor, Containing the Fragrance Composition"; attorney docket No.: 851.32225X00), by the present inventors, the contents of which are incorporated herein by reference in their entirety, it is disclosed that a fragrance composition having enhanced efficacy for masking body malodor (for example, body malodor arising from perspiration in axillary regions of the human body), and which is long-lasting, can be achieved utilizing a composition having (1) the combination of intense (powerful) fruity, aldehydic and green notes, which can form at least part of the top and/or middle notes of the fragrance composition, and (2) acetyl hexamethyl tetralin in an amount of at least 10% by weight (e.g., in the range of 10%–28% by weight), of the total weight of the fragrance composition. This incorporation of, e.g., 10%–28% of acetyl hexamethyl tetralin, in the composition containing the intense fruity, aldehydic and green notes, substantially does not affect the character of the fragrance composition. It is described in this patent application that the fragrance composition including the intense fruity, aldehydic and green notes, and the specified amount of acetyl hexamethyl tetralin, can be included in deodorant compositions, to provide deodorant compositions having enhanced efficacy and that are longlasting.

However, in the disclosed fragrance composition in the concurrently filed application, there is a disclosure that the composition include each of intense fruity, aldehydic and green notes in addition to the acetyl hexamethyl tetralin in the above-referred-to amount. This disclosed composition in the concurrently filed application does not provide complete freedom in choice of the fragrance materials (that is, the materials which contribute to the overall fragrance).

Notwithstanding all of the foregoing, it is still desired to provide a fragrance composition which is capable of masking, e.g., body malodor with enhanced efficacy, for extended periods of time (for example, at least 24 hours), substantially independent of materials (other than a fixative) utilized for forming the fragrance composition.

It is desired to provide such fragrance composition as part of a deodorant for the body (for example, for the human body), including as part of a deodorant composition for axillary regions of the body, to overcome (mask) body malodor.

SUMMARY OF THE INVENTION

Accordingly, it is an object of the present invention to provide a fragrance composition, having enhanced efficacy for masking malodor (e.g., body malodor, including malodor arising in human axillary regions due to, for example, bacteria acting on perspiration) for an extended period of time, substantially irrespective of materials contributing to the top note and/or middle note and/or bottom note of the fragrance composition.

It is a further object of the present invention to provide a fragrance composition which maintains its fragrance, including the fragrance of the top, middle and bottom notes thereof, over extended periods of time, irrespective of materials utilized as top, middle and bottom notes of the fragrance composition.

It is a further object of the present invention to provide a fragrance composition, which masks body malodor for extended periods of time and with enhanced efficacy, irrespective of fragrance materials utilized for providing the top, middle and bottom notes, which can be incorporated in a deodorant composition that contains, or does not contain, polyethylene imine.

It is a still further object of the present invention to provide a deodorant composition, including a deodorant composition for personal care products (such as body or underarm deodorants or soaps), for overcoming (masking) body malodor (such as malodor arising in the axillary region of the human body), which deodorant composition includes a fragrance composition having an enhanced effect in masking malodor (for example, body malodor) over extended periods of time, irrespective of the materials used for the top, middle and bottom notes used in the fragrance composition.

It is a still further object of the present invention to provide a deodorant composition that does or does not contain polyethylene imine, for application to, e.g., the human body, the deodorant composition including a fragrance composition that masks body malodor, the fragrance composition in the deodorant composition having enhanced efficacy for masking malodor and being long lasting, and which has such enhanced efficacy for extended time periods irrespective of the top, middle and bottom notes used in the composition.

It is a still further object of the present invention to provide a fragrance composition providing a more substantive fragrance on skin of a human in, for example, axillary regions of the human body, irrespective of top, middle and bottom notes utilized in the fragrance composition.

The foregoing objects are achieved according to the present invention, by a fragrance composition that includes acetyl hexamethyl tetralin in an amount of more than 28%, and up to 95%, of the total weight of the fragrance composition. The remainder of the fragrance composition includes other fragrancing materials, including at least one of (a) materials providing a top note, (b) materials providing a middle note, and (c) materials forming a bottom note, in an olfactory effective quantity.

Preferably, the fragrance composition according to the present invention includes, in addition to the specified amount of acetyl hexamethyl tetralin, materials providing a top note, materials providing a middle note and additional materials contributing to the bottom note, so as to provide a balanced fragrance having a desired bouquet.

The name "acetyl hexamethyl tetralin" is the name designated in the *CTFA International Cosmetic Ingredient Dictionary* (4th Ed. 1991) for the compound having the empirical formula $C_{18}H_{26}O$ and that conforms to the following structural formula:

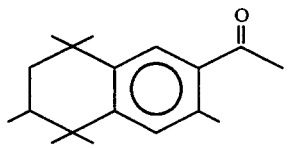

Other structural names for this compound include 6-acetyl-1,1,2,4,4,7-hexamethyl-1,2,3,4-tetrahydronaphthalene and 1-(5,6,7,8-tetrahydro-3,5,5,6,8,8-hexamethyl-2-naphthalenyl)ethanone. Illustrative names for this compound include "Tonalid", from Hercules, Inc (Fragrance and Food Ingredients Group), and "Tetralide", from Bush Boake Allen Ltd (Aroma & Terpene Products). "Tonalid" is an aromatic chemical having a very powerful, warm and radiant substantive musk odor, having a white to off-white solid appearance. This material has a melting point of about 54° C. minimum, and is very stable in acidic and alkaline media.

Acetyl hexamethyl tetralin is a material known to contribute to bottom notes of fragrance compositions. In the fragrance composition according to the present invention, the acetyl hexamethyl tetralin constitutes a material contributing to at least part of the bottom note of the fragrance composition, in the specified amount relative to the total fragrance composition. Thus, in compositions containing the relatively large amounts of acetyl hexamethyl tetralin as in the present invention the acetyl hexamethyl tetralin has an odor impact. However, in order to provide a more complete bouquet, it is preferred that the composition include other materials contributing to the bottom note, such as (but not limited to) galaxolide (1,3,4,6,7,8-hexahydro-4,6,6,7,8,8-hexamethyl-cyclopenta-gamma-2-benzopyran), hexyl cinnamic aldehyde, etc. The bottom note, in total, should be at least 40% by weight of the total weight of the fragrance composition.

The acetyl hexamethyl tetralin not only has an odor impact itself, it also maintains the top and middle notes for a longer time. The acetyl hexamethyl tetralin increases the presence of the top and middle notes in the fragrance 24 hours after application, as compared to fragrance compositions containing lesser amounts of acetyl hexamethyl tetralin.

The fragrance composition can also include diluents and/or solvents, such as (but not limited to) benzyl benzoate, diethyl phthalate, dipropylene glycol, etc.

The materials providing the top note and the middle note are not limited to specific materials (and are not limited to materials providing any specific fragrances), leaving greater creativity in the hands of the perfumer. Known fragrance materials can be utilized to provide the top and middle notes, and to contribute to the bottom note (along with the acetyl hexamethyl tetralin). Examples of such materials are described in the previously discussed U.S. Pat. Nos. to Kuznitz, et al, 5,198,218, and to King, 4,849,400, the contents of each of which have been incorporated herein by reference in their entirety. Note that U.S. Pat. No. 5,198,218 discloses specific fragrance compositions (including top, middle and bottom notes), while No. 4,849,400 discloses various of the classifications (notes) into which most fragrance compositions fall, as well as subclassifications of the more popular fragrance classes.

More or less top note can be incorporated in the fragrance composition, depending on the initial impact desired. Moreover, as within the skill of the perfumer, the notes can be mixed to form a balanced fragrance. Of course, in forming the fragrance, it must be kept in mind that the composition will include more than 28% by weight acetyl hexamethyl tetralin, and thus will include a relatively significant bottom note.

In connection with compounds that can be utilized for providing the top and middle notes, as well as compounds (in addition to acetyl hexamethyl tetralin) contributing to the bottom note, see U.S. Pat. No. 4,304,679 to Hooper, et al, the contents of which are incorporated herein by reference in their entirety. This patent discloses six classes of deodorant (deoperfume) components, as discussed previously in this application; and sets forth specific compounds which fall within these six classes. Also of interest in U.S. Pat. No. 4,304,679 is the specific deodorant compositions set forth in this patent.

All of the top, middle and bottom note materials, together with the required amount of acetyl hexamethyl tetralin, are blended to form the total fragrance. It is preferred that the bottom note materials in addition to the acetyl hexamethyl tetralin, as well as the other note materials, are materials that are residual and substantive. For example, it is preferred to use long-lasting, natural fragrance materials, rather than synthetic fragrances. By incorporating preferred fragrance materials with the acetyl hexamethyl tetralin, an even more efficacious and longer-lasting fragrance composition is produced.

By including the acetyl hexamethyl tetralin compound in the fragrance composition containing materials providing at least one of top note and middle note and another bottom note components, the acetyl hexamethyl tetralin compound being incorporated in an amount more than 28%, and up to (and including) 95%, by weight, of the total weight of the fragrance composition, the fragrance (aroma) including the top and/or middle and/or bottom notes is maintained over extended periods of time; and the fragrance composition can mask malodor (for example, body malodor) with enhanced efficacy, over extended periods of time. Thus, the large amount of acetyl hexamethyl tetralin, of more than 28% by weight of the fragrance composition, acts to extend duration of the fragrance, including top and middle notes, as compared to a same fragrance composition not containing large amounts of acetyl hexamethyl tetralin.

When bottom note compounds such as galaxolide are utilized in relatively large amounts (even in amounts as large as more than 30% by weight, of the total weight of the fragrance composition) with materials providing top and/or middle notes, even with relatively small amounts of acetyl hexamethyl tetralin (e.g., less than 10% by weight, of the total weight of the composition), such enhanced odor masking efficacy over extended periods of time is not achieved. The present invention, utilizing the acetyl hexamethyl tetralin in the specified amounts, provides the objectives of a high efficacy malodor masking, over extended periods of time, irrespective of materials utilized for top and middle notes, or other materials used for the bottom note.

The objectives according to the present invention are also achieved by incorporating the aforementioned fragrance composition, in, e.g., a deodorant effective amount, in a deodorant composition, for application to, for example, the human body. In this deodorant composition, the fragrance composition acts as a deodorant active material, to mask malodor so as to achieve a deodorant effect. This deodorant composition can be one that does not contain polyethylene imine, although the deodorant composition can also include polyethylene imine.

Various other deodorant active materials, such as bacteriostats, in effective amounts, can also be incorporated in the deodorant composition according to the present invention, while still achieving the objectives of the present invention. Thus, the deodorant composition according to the present invention provides enhanced odor masking efficacy over extended periods of time; and can be utilized as a deodorant for axillary regions of the human body, to mask axillary malodor arising due to bacterial action on axillary perspiration.

The objectives according to the present invention are further achieved by a method which includes incorporating the above-described relatively large amounts of acetyl hexamethyl tetralin in a fragrance composition containing materials providing at least one of top note, middle note, and bottom note so as to extend the time period that the fragrance composition is effective, while also providing enhanced odor masking efficacy.

Accordingly, by including the above-described amounts of acetyl hexamethyl tetralin in a fragrance composition together with materials providing at least one of top note, middle note and bottom note, enhanced efficacy in masking malodor (including body malodor, such as body malodor arising from human axillary regions, e.g., arising from bacteria acting on perspiration in the axillary regions) can be achieved, with the enhanced efficacy being maintained over extended periods of time. By incorporating the aforementioned fragrance composition in a deodorant composition, for example, for application to the human body (e.g., to the skin), malodors can be masked over extended time periods, and improved substantive fragrances can be provided for personal care formulations.

DETAILED DESCRIPTION OF THE INVENTION

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present disclosure, where compositions are described as including or comprising specific components, it is contemplated that compositions of the present invention also consist essentially of, or consist of, the recited components. Accordingly, throughout the present disclosure any described composition can consist essentially of, or consist of, the recited components.

The present invention contemplates a fragrance composition incorporating more than 28% by weight, and up to (and including) 95% by weight, of the total weight of the fragrance composition, of acetyl hexamethyl tetralin in the fragrance composition, the fragrance composition also including materials providing at least one of a top note and/or a middle note and/or a bottom note to the fragrance composition. Preferably, the fragrance composition includes acetyl hexamethyl tetralin in an amount of more than 30%, and up to (and including) 95%, more preferably 35%–80%, by weight, of the total weight of the fragrance composition. An illustrative specific amount of acetyl hexamethyl tetralin in fragrance compositions includes 37.5% by weight; of course, the present invention is not limited to this illustrative specific amount.

The materials providing the top note and/or middle note, as well as materials further contributing to the bottom note, can be those known fragrance materials as disclosed, for example, in U.S. Pat. No. 5,198,218 to Kuznitz, et al and U.S. Pat. No. 4,304,679 to Hooper, et al, the contents of each of which have been previously been incorporated herein by reference in their entirety.

Of particular interest are the fragrance compositions disclosed in U.S. Pat. No. 5,198,218, which are compositions which have been formulated into base deodorant stick compositions. These fragrance compositions can be modified according to the present invention, to include relatively large amounts of acetyl hexamethyl tetralin according to the present invention.

The overall fragrance character of the fragrance composition according to the present invention need not be of any special type; for example, need not be fruity or aldehydic or green. Moreover, contrary to the concurrently filed U.S. patent application entitled "Enhanced Efficacy, Long-Lasting Fragrance Composition, and Deodorant Composition, for Masking Malodor, Containing the Fragrance Composition", by the present inventors (attorney docket no.: 851.32225X00), the fragrance composition need not contain any specific class of fragrance note, such as, e.g., the intense fruity, intense green and intense aldehydic notes described in such concurrently filed application (although the fragrance composition of the present invention may contain all or some of such notes). Thus, according to the present invention the creativity of the perfumer is free to combine various fragrance materials so as to provide a desired overall fragrance character.

The composition can include other materials contributing to the bottom note, in addition to the acetyl hexamethyl tetralin, as mentioned previously. Desirably, a plurality of ingredients are utilized to form the bottom note, so as to provide an improved fragrance composition having a well-balanced fragrance.

As seen in the foregoing, the perfumer is free to utilize various notes, within the scope of the present invention, so as to achieve desired fragrance character. The fragrance composition can include ingredients providing various notes of the fragrance families (for example, green notes, fruity notes, aldehydic notes, chypre notes, oriental notes, tobacco notes, leather notes and fougère notes), and sub-classifications thereof (such as fresh and balsamic green notes; fresh and sweet floral notes; floral and floral-woody-powdery aldehydic notes; and fresh-mossy-aldehydic, floral-mossy-animalic and mossy-fruity chypre notes).

In general, there is substantially no limitation on amounts of the various materials contained in the fragrance composition according to the present invention, other than the specific amount of acetyl hexamethyl tetralin. Generally, it is desired that the fragrance composition include sufficient amounts of the materials contributing to the top, middle and bottom notes such that some of each of the materials remain on the skin in the fragrance composition 24 hours after application of the composition, e.g., to axillary regions (to the skin in axillary regions) of a human body (that is, after 24 hours each of the original fragrance notes has been maintained). By providing a fragrance composition including such amounts of the various materials, a desired masking of malodor is maintained, by the desired fragrance, over extended periods of time (for example, 24 hours).

Adding acetyl hexamethyl tetralin in an amount of 0.75% by weight to an underarm deodorant stick formulation containing 1.0% by weight fragrance improves deodorant efficacy by 19.5% and 23.8% respectively, at 12 and 24 hours after treatment, despite the fact that acetyl hexamethyl tetralin exhibits little detectable fragrance by itself. The foregoing improved deodorant efficacy was found in a deodorant clinical protocol as typically performed at clinical facilities. Therefore, an underarm deodorant composition containing a total of 1.75% by weight fragrance, in which the acetyl hexamethyl tetralin constitutes 42.86% by weight of the total fragrance composition, exhibits superior clinical deodorant performance than the identical formulation containing the identical fragrance, but without the acetyl hexamethyl tetralin.

On the other hand, adding another long-lasting, substantive fragrance ingredient such as galaxolide, in an amount of 0.5% by weight, to an underarm deodorant formulation containing 1.0% fragrance, does not result in superior clinical performance. Such a formulation exhibited clinical performance at statistical parity to the formulation without the galaxolide.

The foregoing shows that inclusion of acetyl hexamethyl tetralin, in particular, in the recited amount, rather than inclusion of substantive fragrance ingredients (acting as a bottom note material) such as galaxolide in the recited amounts, achieves the objectives of the present invention.

The present invention also contemplates deodorant compositions having incorporated therein the above-described fragrance composition, in, e.g., deodorant effective amounts. Such deodorant composition can, illustratively, be a composition to be applied to the human body (for example, to the skin, in axillary regions of the human body). By using the deodorant composition according to the present invention as an axillary deodorant, malodor in the axillary region can be masked for extended periods of time (for example, at least 24 hours).

The deodorant composition according to the present invention can utilize any conventional vehicle effective for application to the body (for example, to the skin of a human). For example, the vehicle can be a vehicle for a stick deodorant, an aerosol deodorant, a roll-on, a spray, etc. Such vehicles are well known in the art.

The fragrance compositions according to the present invention are included in the deodorant composition of the present invention, together with the vehicle, in amounts corresponding to amounts of conventional fragrance compositions incorporated in known deodorant compositions.

Other known deodorant active agents can be incorporated in the deodorant composition according to the present invention, in effective amounts. For example, bacteriostats, illustrated by Triclosan (*CTFA International Cosmetic Ingredient Dictionary* (4th Ed. 1991)), can be incorporated in the deodorant composition to provide even further deodorant protection.

The fragrance composition can be made by mixing the various ingredients to come up with the desired final bouquet or aroma. Generally, the more volatile materials are incorporated near the end of the manufacturing process, to avoid volatilization of ingredients from the composition. More than 28% by weight, and up to (and including) 95% by weight, of acetyl hexamethyl tetralin, is mixed with the remaining ingredients, to achieve the objective of a long-lasting fragrance with enhanced efficacy for masking malodor.

The deodorant composition according to the present invention is produced by the same processing steps as used in producing prior deodorant compositions, with the fragrance composition according to the present invention being substituted for previous, conventional fragrance compositions. It is desired that the fragrance composition be added near the end of the deodorant composition manufacturing procedure, in order to avoid volatilization of fragrance components, particularly where heating is utilized in forming the deodorant composition (for example, in melting solid ingredients of the vehicle in forming a stick deodorant).

Generally, deodorant compositions according to the present invention are used by, e.g., the consumer in a same manner as done conventionally. For example, with a deodorant composition, including the fragrance composition, of the present invention, in the form of a stick, the stick is elevated out of a dispensing package such that an end of the stick deodorant is exposed, and the stick deodorant is then rubbed on the axillary region of the body so as to leave a thin film of the deodorant composition on the skin in the axillary region, so as to provide deodorant protection.

It is preferred that the stick product, or any other deodorant composition (such as aerosol, roll-on, etc.) apply at least 0.3 grams of product per 4 inch square, so as to apply an effective amount of the fragrance on the skin.

The following Examples further describe and demonstrate embodiments within the scope of the present invention. These Examples are given solely for the purpose of illustration and are not to be construed as limitations of the invention. The first two Examples illustrate fragrance compositions according to the present invention, while the third Example illustrates what would be a deodorant composition (a stick deodorant) according to the present invention, which can appropriately include a fragrance composition according to the present invention. Many variations of these Examples are possible without departing from the spirit and scope of the present invention.

In the following Examples 1 and 2, the amounts are in parts by weight. In Example 3, the amounts are in percent by weight, of the total weight of the deodorant composition.

| EXAMPLE 1 | |
|---|---|
| Benzyl Acetate | 500.00 |
| Cedarwood Texas Light | 500.00 |
| Cinnamic Alcohol | 20.00 |
| Coriander Oil | 40.00 |
| Coumarin | 80.00 |
| Cypress Oil | 80.00 |
| Dipropylene Glycol | 2000.00 |
| Ethyl Vanillin | 10.00 |
| Galaxolide 50 | 910.00 |
| Geranium Bourbon Synthetic | 40.00 |
| Hydrocarbon B Resin | 10.00 |
| Lavender Oil 40/42 | 300.00 |
| Linalyl Acetate Synthetic | 1000.00 |
| Mousse De Metra | 10.00 |
| Myrrh Coeur @ 50.0% dipropylene glycol | 40.00 |
| Olibanum Resin | 40.00 |
| Patchouly Oil M/D | 250.00 |
| Phenyl Ethyl Alcohol | 150.00 |
| Thyme NF White Extra | 10.00 |
| "Tonalid" | 4000.00 |
| Wormwood Oil | 10.00 |
| TOTALS: | 10000.00 |
| EXAMPLE 2 | |
| Aldehyde C-11 Undecylenic | 13.00 |
| Allyl Amyl Glycolate | 120.00 |
| Benzyl Salicylate | 500.00 |
| Dihydro Myrcenol | 1580.00 |
| Dipropylene Glycol | 1000.00 |
| Galaxolide 50 B.B. | 1320.00 |
| Galbanum Oil | 13.00 |
| Grisalva | 13.00 |
| Hedione | 130.00 |
| Hexyl Cinnamic Aldehyde | 450.00 |
| Phenyl Ethyl Alcohol | 500.00 |
| Rose Oxide | 10.00 |
| Sandalwood Oil E.I. | 100.00 |
| "Tonalid" | 4000.00 |
| Vertenex | 13.00 |
| Vertofix Coeur | 238.00 |
| TOTALS: | 10000.00 |
| EXAMPLE 3 | |
| Constituent | Amount |
| Sodium stearate | 7.0% |
| Propylene glycol | 70.0% |
| Water | 20.7% |
| Triclosan | 0.3% |
| Fragrance composition of the present invention | 2.0% |

As seen in Example 3, the fragrance composition according to the present invention can be incorporated in stick deodorants. Illustratively, stick deodorants according to the present invention can include constituents, and amounts, as set forth in the following Table 1.

TABLE 1

| Constituent | Amount | Preferred |
|---|---|---|
| Sodium stearate | 5–8% | 6–7% |
| Propylene glycol | 30–75% | 50–70% |
| Dipropylene glycol | 0–40% | — |
| Water | 5–30% | 15–25% |
| Triclosan | 0–0.5% | 0.2–0.3% |
| Fragrance composition of the present invention | 0.25–2.5% | 1.25–2.0% |

The foregoing Table 1 sets forth illustrative constituents and amounts, including more general and preferred amounts. This Table 1 is illustrative and not limiting to the present invention. More generally, the fragrance composition of the present invention, with or without additional deodorant active agents such as Triclosan, can be incorporated in stick base compositions such as a polyhydric alcohol gelled with a soap. For example, the polyhydric alcohol can have 2–6 carbon atoms and 2–6 hydroxyl groups, and the soap can be a sodium salt of a $C_{12}$ to $C_{22}$ fatty acid.

As seen in the foregoing, deodorant compositions according to the present invention include fragrance compositions, with or without additional deodorant active materials such as Triclosan. Thus, according to the deodorant composition of the present invention the fragrance composition acts as an active deodorant agent, for example, without other active deodorant agents, such as sodium bicarbonate, and without, for example, polyethylene imine. Various of these other active deodorant agents can be incorporated in deodorant compositions having fragrance compositions according to the present invention.

Accordingly, through the present invention, a deodorant composition which is long-lasting and which has enhanced efficacy in masking malodor, and without restriction as to fragrancing ingredients which must be included in the composition, is achieved.

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

We claim:

1. A fragrance composition for masking malodor, adapted to be applied to a human, the malodor being human malodor, comprising fragrance materials providing at least one of top note and middle note and bottom note, in an olfactory effective quantity of said fragrance materials providing said at least one of top note and middle note and bottom note, wherein more than an amount of 28% by weight, and up to 95% by weight, of the total weight of the fragrance composition, is 6-acetyl-1,1,2,4,4,7-hexamethyl-1,2,3,4-tetrahydronaphthalene, so as to enhance efficacy for extended periods of time.

2. The fragrance composition according to claim 1, wherein 6-acetyl-1,1,2,4,4,7-hexamethyl-1,2,3,4-tetrahydronaphthalene is included in the fragrance composition in an amount of 35%–80% of the total weight of the fragrance composition.

3. The fragrance composition according to claim 1, wherein the fragrance composition includes fragrance materials providing a top note, fragrance materials providing a middle note and fragrance materials providing a bottom note.

4. The fragrance composition according to claim 3, wherein the 6-acetyl-1,1,2,4,4,7-hexamethyl-1,2,3,4-tetrahydronaphthalene contributes to the bottom note of the fragrance composition, and the fragrance composition includes additional fragrance materials contributing to the bottom note.

5. The fragrance composition according to claim 4, wherein said additional fragrance materials contributing to the bottom note are at least one selected from the group consisting of 1,3,4,6,7,8-hexahydro-4,6,6,7,8,8-hexamethy-cyclopenta-gamma-2-benzopyran and hexyl cinnamic aldehyde.

6. The fragrance composition according to claim 4, wherein all fragrance materials contributing to the bottom note constitute at least 40% by weight of the total weight of the composition.

7. The fragrance composition according to claim 4, wherein the fragrance composition includes at least one of a diluent and a solvent.

8. The fragrance composition according to claim 7, wherein said at least one of a diluent and a solvent is selected from the group consisting of benzyl benzoate, dipropylene glycol and diethyl phthalate.

9. The fragrance composition according to claim 1, wherein the fragrance composition is to be applied to axillary regions of a human, the malodor being axillary malodor.

10. A deodorant composition for masking malodor, comprising the fragrance composition according to claim 1, in a deodorant effective amount, in a vehicle effective for applying the fragrance composition to a body.

11. The deodorant composition according to claim 10, further including a deodorant active material in addition to the fragrance composition.

12. The deodorant composition according to claim 11, wherein the deodorant active material includes Triclosan.

13. The deodorant composition according to claim 10, wherein said body is a human, the malodor being human malodor.

14. The deodorant composition according to claim 13, wherein said body is axillary regions of the human, the malodor being axillary malodor.

15. The deodorant composition according to claim 14, wherein the vehicle is a stick base composition.

16. The deodorant composition according to claim 15, wherein the stick base composition includes a polyhydric alcohol gelled with a soap.

17. The deodorant composition according to claim 16, wherein the polyhydric alcohol has 2 to 6 carbon atoms and 2 to 6 hydroxyl groups, and the soap is a sodium salt of a $C_{12}$ to $C_{22}$ fatty acid.

18. A deodorant composition for masking malodor, comprising the fragrance composition according to claim 3, in a deodorant effective amount, in a vehicle effective for applying the fragrance composition to a body.

19. The deodorant composition according to claim 18, wherein said body is axillary regions of the human, the malodor being axillary malodor.

20. A deodorant composition for masking malodor, comprising the fragrance composition according to claim 6, in a deodorant effective amount, in a vehicle effective for applying the fragrance composition to a body.

21. The deodorant composition according to claim 20, wherein said body is axillary regions of the human, the malodor being axillary malodor.

22. A method of extending the time period over which a fragrance composition provides malodor masking, comprising a step of incorporating (a) 6-acetyl-1,1,2,4,4,7-hexamethyl-1,2,3,4-tetrahydronaphthalene, in an amount more than 28%, and up to 95%, by weight, of the total weight of the fragrance composition, with (b) fragrance materials providing at least one of top note and middle note and bottom note, so as to form the fragrance composition, the fragrance materials being present in an olfactory effective amount.

23. The method according to claim 22, wherein the 6-acetyl-1,1,2,4,4,7-hexamethyl-1,2,3,4-tetrahydronaphthalene is incorporated in an amount of 35%–80% by weight, of the total weight of the composition.

24. The method according to claim 22, wherein said fragrance materials provide a top note and a middle note and a bottom note.

25. The method according to claim 24, wherein the 6-acetyl-1,1,2,4,4,7-hexamethyl-1,2,3,4-tetrahydronaphthalene contributes to the bottom note, the fragrance composition containing additional fragrance materials that also contribute to the bottom note.

26. The method according to claim 25, wherein the additional fragrance materials that also contribute to the bottom note are at least one selected from the group consisting of 1,3,4,6,7,8-hexahydro-4,6,6,7,8,8-hexamethyl-cyclopenta-gamma-2-benzopyran and hexyl cinnamic aldehyde.

27. The fragrance composition according to claim 1, containing materials providing at least one of top note and middle note, in addition to the 6-acetyl-1,1,2,4,4,7-hexamethyl-1,2,3,4-tetrahydronaphthalene, the amount of 6-acetyl-1,1,2,4,4,7-hexamethyl-1,2,3,4,-tetrahydronaphthalene incorporated in the fragrance composition being sufficient to increase presence of said at least one of top note and middle note in the composition 24 hours after application, as compared to presence of the at least one of top note and middle note 24 hours after application of a fragrance composition containing the at least one of the top note and middle note and containing smaller amounts of 6-acetyl-1,1,2,4,4,7-hexamethyl-1,2,3,4-tetrahydronaphthalene.

28. The fragrance composition according to claim 27, wherein said fragrance materials include materials providing at least one of green notes, fruity notes, aldehydic notes, chypre notes, oriental notes, tobacco notes, leather notes and fougere notes.

29. The fragrance composition according to claim 27, wherein the fragrance composition contains a sufficient amount of the fragrance materials providing said at least one of said top note and middle note and said bottom note such that some of each of said fragrance materials remain 24 hours after application.

30. The fragrance composition according to claim 1, wherein said fragrance materials include natural fragrance materials.

31. The fragrance composition according to claim 1, wherein said fragrance materials include materials providing at least one of green notes, fruity notes, aldehydic notes, chypre notes, oriental notes, tobacco notes, leather notes and fougeère notes.

32. The fragrance composition according to claim 1, wherein the fragrance composition contains a sufficient amount of the fragrance materials providing said at least one of said top note and said middle note and said bottom note such that some of each of said fragrance materials remain 24 hours after application.

33. The fragrance composition according to claim 1, wherein the composition is adapted to be incorporated in a deodorant composition for application to the human body.

34. The deodorant composition according to claim 10, containing materials providing at least one of top note and middle note, in addition to the 6-acetyl-1,1,2,4,4,7-hexamethyl-1,2,3,4-tetrahydronaphthalene, the amount of 6-acetyl-1,1,2,4,4,7-hexamethyl-1,2,3,4-tetrahydronaphthalene incorporated in the fragrance composition being sufficient to increase presence of said at least one of top note and middle note in the composition 24 hours after application, as compared to presence of the at least one of top note and middle note 24 hours after application of a fragrance composition containing the at least one of the top note and middle note and containing smaller amounts of 6-acetyl-1,1,2,4,4,7-hexamethyl-1,2,3,4-tetrahydronaphthalene.

35. The deodorant composition according to claim 10, wherein the fragrance composition contains a sufficient amount of the fragrance materials providing said at least one of said top note and said middle note and said bottom note such that some of each of said fragrance materials remain 24 hours after application.

36. The deodorant composition according to claim 10, wherein the fragrance composition contains a sufficient amount of the fragrance materials providing said at least one of said top note and said middle note and said bottom note such that some of each of said fragrance materials remain 24 hours after application.

37. The method according to claim 22, wherein said fragrance materials provide at least one of top note and middle note, and wherein the amount of 6-acetyl-1,1,2,4,4,7-hexamethyl-1,2,3,4-tetrahydronaphthalene incorporated in the fragrance composition is sufficient to increase presence of said at least one of top note and middle note in the composition 24 hours after application, as compared to presence of the at least one of top note and middle note 24 hours after application of a fragrance composition containing the at least one of the top note and middle note and containing smaller amounts of 6-acetyl-1,1,2,4,4,7-hexamethyl-1,2,3,4-tetrahydronaphthalene.

38. The method according to claim 22, wherein the fragrance composition contains a sufficient amount of the fragrance materials providing said at least one of said top note and said middle note and said bottom note such that some of each of said fragrance materials remain 24 hours after application.

* * * * *